United States Patent [19]

Kawai et al.

[11] Patent Number: 4,812,441
[45] Date of Patent: Mar. 14, 1989

[54] HYPOCHOLESTEROLEMICALLY ACTIVE PROTEIN DERIVED FROM STREPTOCOCCUS

[75] Inventors: Yasuo Kawai, Atsugi; Kazunaga Yazawa, Sagamihara, both of Japan

[73] Assignee: Kabushiki Kaisya Advance Kaihatsu Kenkyujo, Tokyo, Japan

[21] Appl. No.: 827,500

[22] Filed: Feb. 7, 1986

Related U.S. Application Data

[63] Continuation of Ser. No. 563,403, Dec. 20, 1983, abandoned.

[30] Foreign Application Priority Data

Dec. 28, 1982 [JP] Japan ................. 57-227395

[51] Int. Cl.$^4$ ............. A61K 37/02; A61K 35/74; C12P 21/00; C12R 1/46
[52] U.S. Cl. ........................... 514/2; 530/825; 514/824; 435/68; 435/272; 435/885
[58] Field of Search ............ 435/68, 272, 885; 530/825; 514/2, 12, 824

[56] References Cited

U.S. PATENT DOCUMENTS

| | | | |
|---|---|---|---|
| 3,567,821 | 3/1971 | Nouvel | 424/93 |
| 4,259,442 | 3/1981 | Gayral | 435/36 |
| 4,357,323 | 11/1982 | Soma et al. | 536/1.1 |
| 4,448,768 | 5/1984 | Colman et al. | 530/825 |
| 4,536,496 | 8/1985 | Shimizu et al. | 514/54 |

FOREIGN PATENT DOCUMENTS

| | | |
|---|---|---|
| A-101209 | 2/1984 | European Pat. Off. |
| A-115157 | 8/1984 | European Pat. Off. |
| A-132981 | 2/1985 | European Pat. Off. |
| 2106154 | 8/1972 | Fed. Rep. of Germany |
| 0122723 | 9/1980 | Japan |
| 56-12318 | 2/1981 | Japan |
| 930107 | 7/1963 | United Kingdom |

OTHER PUBLICATIONS

Rall, Jr. et al, "Human Apolipoprotein E", J. Biological Chemistry, vol. 257(8), 4-25-82, pp. 4171-4178.
Slobodskaya, V., et al, "Comparison of Hypochesterolemic Effect . . . ", Biol Abst. 76(10), 11-15-83.
Watanabe, T., et al, "Studies on Streptococci" Microbiol. Immunol., vol. 25(3), 1981, pp. 257-269.
Moore et al., "Cell–Free Protein Synthesis . . . ", Chem. Abstracts 66:16521u, 1967.
Herson et al, "Protein Synthesis . . . ", Chem. Abstracts, vol. 72, 28377p, 1970.
Rao et al., "Influence of Milk . . . ", Chem. Abstracts, vol. 95, 185927k, 1981.
Salvioli et al., "Bile Acid . . . ", Chem. Abstracts 96:197302m, 1982.
Hussain, et al., "Activation . . . ", Chem. Abstracts 85:137972t, 1976.

(List continued on next page.)

Primary Examiner—Ronald W. Griffin
Assistant Examiner—Nancy S. Carson
Attorney, Agent, or Firm—Finnegan, Henderson, Farabow, Garrett & Dunner

[57] ABSTRACT

A hypocholesterolemically active protein capable of reducing the blood cholesterol in mammals having the following characteristics:

(a) Molecular weight by gel filtration: 30,000±7,000
(b) Isoelectric point: 7.9±0.2
(c) Amino acid composition (mole %):

| Glycine | 25.23 | Alanine | 10.98 |
|---|---|---|---|
| Glutamate | 10.34 | Asparaginate | 8.20 |
| Lysine | 6.39 | Leucine | 5.58 |
| Valine | 5.41 | Isoleucine | 5.18 |
| Threonine | 4.23 | Tyrosine | 4.19 |
| Serine | 3.46 | Proline | 2.62 |
| Arginine | 2.60 | Phenylalanine | 2.51 |
| Methionine | 1.56 | Histidine | 1.30 |
| Cysteine | 0.16 | | |

(d) Pattern of electrophoresis: a sharp band on the anode side on polyacrylamide gel electrophoresis. This hypocholesterolemically active protein is derived from a microorganism belonging to the genus Streptococcus.

9 Claims, 4 Drawing Sheets

OTHER PUBLICATIONS

Imshenetskii et al; Chemical Abstracts, vol. 89:57708d, 1978.

Petrova et al; Chemical Abstracts, vol. 95:199588n, 1981.

Nord et al., "Formation of Glycoside-Hydrolases by Oral Streptococci," Archs. Oral Biol., vol. 18, pp. 391–402, (1973).

Microbiol. Immunol., vol. 25(3), 257–269, 1981.

Microbiol. Immunol., vol. 26(5), 363–373, 1982.

The American Journal of Clinical Nutrition 33: Nov. 1980, pp. 2458–2461.

Infection and Immunity, vol. 19, No. 3, Mar. 1978, pp. 771–778.

The American Journal of Clinical Nutrition 32: Jan. 1979, pp. 187–188.

Mechanisms of Ageing and Development, 16 (1981), 149–158.

Mechanism of Ageing and Development, 17 (1981), 173–182.

Moore et al., "Cell-Free Protein Synthesis", Science, vol. 154, pp. 1350–1353 (1966).

Henson et al., "Protein Synthesis in Cell-Free Extracts of *Streptococcus faecalis*", J. of Bacteriology, vol. 100, pp. 1350–1354 (1969).

Rao et al., "Influence of Milk and *Thermophilus* Milk on Plasma Cholesterol Levels and Hepatic Cholesterogenesis in Rats", J. of Food Science, vol. 46, pp. 1339–1341 (1981).

Salvioli et al., "Bile Acid Transformation by the Intestinal Flora an Cholesterol Saturation in Bile," *Digestion*, vol. 23, pp. 80–88 (1982).

Hussain et al., "Activation of Lipolytic Activity of *Streptococcus faecilis* by Nitrosguanidine", folia *Microbiol.*, vol. 21, pp. 73–74 (1976).

HYPOCHOLESTEROLEMICALLY ACTIVE PROTEIN DERIVED FROM STREPTOCOCCUS

BACKGROUND OF THE INVENTION

1. Field of the Invention

This application is a continuation of application Ser. No. 563,403, filed Dec. 20, 1983, now abandoned.

The present invention relates to a novel hypocholesterolemically active protein (namely, cholesterol-reducing protein abbreviated as "CRP" hereinbelow), a process for preparing the same, a hypocholesterolemic antiatherosclerotic pharmaceutical composition containing the same, and a method for reducing the blood cholesterol in mammals.

2. Description of the Prior Art

As is well-known in the art, today, several pharmaceutical preparations such as clofibrate and its related preparations have been proposed as therapeutical medicines for atherosclerosis or hyperlipidemia, which is one of the so-called typical middle-aged or geriatric diseases. However, the desired purposes are not fully satisfied by these known medicines from the viewpoint of, for example, pharmacological effects and side effects and therefore, the need for developing more effective and safe medicines has remarkably increased.

SUMMARY OF THE INVENTION

Accordingly, an object of the present invention is to provide a novel hypocholesterolemically active protein, CRP, which is safe for the administration into mammals.

Another object of the present invention is to provide a process for preparing a novel protein, CRP, capable of effectively reducing the blood cholesterol in mammals.

A further object of the present invention is to provide a hypocholesterolemic or antiatherosclerotic pharmaceutical composition containing, as an active ingredient, a novel protein, CRP.

A still further object of the present invention is to provide a method for reducing the blood cholesterol in mammals.

Other objects and advantages of the present invention will be apparent from the description set forth hereinbelow.

In accordance with the present invention, there is provided a hypocholesterolemically active protein capable of reducing the blood cholesterol in mammals having the following characteristics:

(a) Molecular weight by gel filtration: 30,000±7,000
(b) Isoelectric point: 7.9±0.2
(c) Amino acid composition (mole %):

| Glycine | 25.23 | Alanine | 10.98 |
|---|---|---|---|
| Glutamate | 10.34 | Asparaginate | 8.20 |
| Lysine | 6.39 | Leucine | 5.58 |
| Valine | 5.41 | Isoleucine | 5.18 |
| Threonine | 4.23 | Tyrosine | 4.19 |
| Serine | 3.46 | Proline | 2.62 |
| Arginine | 2.60 | Phenylalanine | 2.51 |
| Methionine | 1.56 | Histidine | 1.30 |
| Cysteine | 0.16 | | |

(d) Pattern of electrophoresis: a sharp band on the anode side on polyacrylamide gel electrophoresis.

BRIEF DESCRIPTION OF THE DRAWING

The present invention will be better understood from the description set forth below with reference to the accompanying drawings, in which.

DESCRIPTION OF THE PREFERRED EMBODIMENTS

The present inventors have found that a novel protein obtained from microorganisms belonging to the genus Streptococcus and/or the supernatant of culture broth can effectively reduce the blood cholesterol, and that this constituent extracted from these so-called gastrointestinal bacteria and the supernatant of culture broth is substantially nontoxic when orally administered.

The microorganisms used in the preparation of the product, the manufacturing methods, the physicochemical characteristics, and the pharmacological effects of the CRP protein according to the present invention will now be shown in detail hereinbelow.

Microorganisms

1. Species

Microorganisms utilizable in the present invention belonging to the genus *Streptococcus*: *Streptococcus faecium*, *Streptococcus faecalis*, *Streptococcus bovis*, *Streptococcus avium*, *Streptococcus durans*, *Streptococcus salivarius*, *Streptococcus mitis*, *Streptococcus equinus*, and others, are preferably shown. Besides, the species defined as indigenous intestinal streptococci are preferably included.

Typical examples of such microorganisms isolated from healthy human feces have been deposited since July 15, 1982 in the Fermentation Research Institute (FRI) in Japan (all the numbers quoted as "FERM-P" in Table 1 refer to the deposition numbers of said Institute) and transferred to the Fermentation Research Institute (FRI) (i.e., International Depository Authority under Budapest Treaty in Japan) as the following FERM-BP deposition numbers in Table 1 under Budapest Treaty on the International Recognition of the Deposit of Microorganisms for the Purpose of Patent Procedure:

TABLE 1

| Name of strain | Deposition number | | |
|---|---|---|---|
| Streptococcus faecium | ADV1009 | FERM P-6624 | FERM BP-296 |
| Streptococcus faecalis | ADV9001 | FERM P-6625 | FERM BP-297 |
| Streptococcus avium | AD2003 | FERM P-6626 | FERM BP-298 |
| Streptococcus salivarius | ADV10001 | FERM P-6627 | FERM BP-299 |
| Streptococcus durans | ADV3001 | FERM P-6628 | FERM BP-300 |
| Streptococcus mitis | ADV7001 | FERM P-6629 | FERM BP-301 |
| Streptococcus equinus | ADV8001 | FERM P-6630 | FERM BP-302 |

2. Microbiological characteristics of microorganisms

General microbiological characteristics

The microbiological characteristics of the microorganisms in the present invention are the same as those of known microorganisms belonging to the identical class.

That is, the general microbiological characteristics, cultivating methods, and other properties correspond to those described in the following literatures:

(1) Bergey's Manual of Determinative Bacteriology, 8th ed., 490-509 (1974)
(2) Int. J. Syst. Bact. 16, 114 (1966).
(3) Microbiol. Immunol. 25 (3), 257-269 (1981)
(4) J. Clin. Pathol. 33, 53-57. (1980)
(5) J. General Microbiol. 128, 713-720 (1982)
(6) Applied Microbiol. 23 (6), 1131-1139 (1972).

The typical microbiological properties of the above-exemplified strains according to the present invention can be summarized as follows (Table 2):

TABLE 2

| Characteristics | ADV 1009 | ADV 9001 | AD 2003 | ADV 10001 | ADV 3001 | ADV 7001 | ADV 8001 |
|---|---|---|---|---|---|---|---|
| Shape of cell | | | | spheroid | | | |
| Gram stain | + | + | + | + | + | + | + |
| Hemolysis | α | α | α | α | α | α | α |
| Growth at 10° C. | + | + | ± | – | + | – | – |
| Growth at 45° C. | + | + | + | ± | + | ± | + |
| Growth at 50° C. | + | – | – | – | + | – | – |
| Thermal resistance at 60° C. for 30 min | + | + | + | – | + | – | – |
| Growth in culture medium at pH 9.6 | + | + | + | – | + | – | – |
| Methylene blue reduction ability | + | + | – | – | + | – | – |
| Liquefaction of gelatin | – | – | – | – | – | – | – |
| Growth in culture medium containing NaCl (6.5%) | + | + | – | – | + | – | – |
| Growth in culture medium containing bile (40%) | + | + | + | – | + | – | + |
| Productivity of ammonia | + | + | ND*2 | – | + | ± | – |
| Hydrolysis of hippuric acid | – | ± | – | – | + | – | – |
| Growth in culture medium containing tellurite | – | + | – | ND | – | ND | – |
| Growth in culture medium containing TTC*1 | – | + | – | ND | – | ND | – |
| Acid production from carbon source | | | | | | | |
| Glucose | + | + | + | + | + | + | + |
| Esculin | ± | + | + | + | ± | ND | + |
| Inulin | – | – | – | + | – | – | ± |
| Lactose | + | + | + | ± | + | ± | – |
| Glycerol | – | + | ± | – | – | – | – |
| Arabinose | + | – | + | – | – | – | – |
| Melezitose | – | + | ± | ND | – | ND | – |
| Sorbitol | – | + | + | – | – | – | – |
| Antigenic group | D | D | Q(D) | K | D | – | D |

*1 2,3,5-triphenyltetrazolium chloride.
*2 Not done

3. Cultivating methods

The cultivation of these microoganisms is conventional. For example, the bacterial cells can be collected by stationary cultivation in Rogosa broth medium having the following composition under an aerobic condition, and can be harvested by centrifugation of the culture.

| Composition of Rogosa Broth Medium | |
|---|---|
| Trypticase | 10 g |
| Yeast extract | 5 g |
| Tryptose | 3 g |
| $K_2HPO_4$ | 3 g |
| $KH_2PO_4$ | 3 g |
| Triammonium citrate | 2 g |
| Tween 80 | 1 g |
| Glucose | 20 g |
| Cysteine hydrochloride | 0.2 g |
| Salt solution*1 | 5 ml |
| Distilled water | to 1 liter |
| (pH 7, heat sterilization at 121° C. for 15 minutes) | |
| *1 $MgSO_4.7H_2O$ | 11.5 g |
| $FeSO_4.7H_2O$ | 0.68 g |
| $MnSO_4.2H_2O$ | 2.4 g |
| Distilled water | 100 ml |

Preparation of the CRP protein

An example of the typical preparation procedures of the said CRP protein in the present invention is outlined as follows:

1. Collection of microorganisms

Each of the microbial strains shown above is inoculated into Rogosa broth medium, incubated without agitation at 37° C. for 5 to 10 hours under an aerobic condition to yield a subsequent culture broth at a certain viable bacterial cell concentration. The culture broth is continuously centrifuged at 12,000 rpm. The harvested bacterial cells are then washed in saline (0.85% NaCl) 2 to 3 times.

2. Disruption of bacterial cells (a) The washed cells were suspended in physiological saline and heat-treated at 115° C. for 10 minutes to be disrupted.

(b) The bacterial cells washed and suspended in physiological saline are disrupted by sonication, French press, and other conventional methods.

3. Removal of fat from the cell

The disrupted cell suspension is mixed with chloroform-methanol (2:1, v/v). The components extractable by the organic solvent are then completely removed by centrifugation at 3,000 rpm for 10 minutes and the chloroform layer is discarded.

4. Treatment with proteolytic enzymes

The defatted sample mentioned above is treated with proteolytic enzymes such as pronase, trypsin, and pepsin under ordinary procedures. Of these proteolytic enzymes, pronase is most useful for the purpose. The conditions of the treatment with this enzyme are referred to in the following literature: Methods in Enzymology, Vol. VIII, p. 26 (1966).

5. Purification

The centrifugal supernatant of the proteolytic reaction mixture is added with precipitants such as trichloroacetic acid, or ammonium sulfate to precipitate the protein fraction. The protein fraction is then treated with appropriate nucleases to remove nucleic acid constituents such as DNA and RNA in the fraction. Dialysis is repeatedly carried out after such enzymatic treatments.

The partly purified protein fraction is then subjected to a repetition of further purification procedures such as gel filtration and ammonium sulfate fractionation, and finally a pure preparation of protein designated as the CRP protein is obtained.

The CRP protein can be prepared, generally, according to its physicochemical characteristics, as mentioned below, by such a lot of isolation and purification procedures widely employed in the field concerned, such as precipitation-dissolution and extraction, solvent extraction, dialysis, column chromatography, electrophoresis, gel filtration, or combination of them. Therefore, the present invention is by no means limited to the specified procedures.

That is, the present invention is in relation to the preparation methods of hypocholesterolemically active products which are composed of protein and obtained from microorganisms belonging to the genus Streptococcus, because the pharmacological activity is found in the protein fraction. This is described in each example hereinbelow in detail.

Besides, hypocholesterolemic activity in the supernatant of the culture broth is about 1/5 of that in the bacterial cell.

Physicochemical characteristics of the CRP protein

Physicochemical and physiological characteristics of the CRP protein of the present invention are shown as follows.

1. Chemical nature and solubilizing properties

The powdered sample used after desalting and freeze-drying was non-deliquescent white powder and was very soluble in water, and was soluble in acetone. When the solution of the CRP protein was mixed with ammonium sulfate or trichroloacetic acid in the cold (4° C.), turbidity and precipitation were observed, respectively.

2. Molecular weight

The molecular weight of the CRP protein was estimated at 30,000±7,000 by gel filtration using a Toyopearl HW 55 column (Toyosoda Co., Ltd.) equilibrated with 25 mM of Tris-HCl buffer containing 0.3 M NaCl (pH 7.5).

3. Isoelectric point

The isoelectric point of the CRP protein was measured by the isoelectric focusing method using 5% polyacrylamide gel containing Ampholine (pH 3.5 to 10, LKB Co., Ltd.) at the final concentration of 2% at 4° C. under a stable voltage of 200 V for 3 hrs. 0.02 M $H_3PO_4$ and 1 M NaCl solutions were used for the electrode solutions of the anode and the cathode, respectively.

The sample (100 g) was applied and staining was made by Coomassie Brilliant Blue R-250. The isoelectric point was 7.9±0.2. This was between those of the reference proteins of rat hemoglobin and sperm whale myoglobin.

4. Amino acid composition

The sample (1 mg) was suspended in 1 ml of 6 N HCl and introduced into an ampoule, frozen in dry ice-methanol, and the air was replaced by $N_2$ gas in vacuo. The gas replacement was repeated 3 times and the ampoule was sealed in vacuo. After hydrolysis at 110° C. for 24 hours in a heating block, hydrochloride was removed by rotary evaporation in vacuo, and the sample was dissolved in 200 $\mu l$ of 1/50 N HCl. Then, 50 $\mu l$ of this sample was analysed by an amino acid analyser (Model 835 High Speed Amino Acid Analyzer, Hitachi, Ltd.) The amino acid composition of the sample (the CRP protein) is shown in Table 3.

TABLE 3

| Amino acid | (mole %) |
| --- | --- |
| Glycine | 25.23 |
| Alanine | 10.98 |
| Glutamate | 10.34 |
| Asparaginate | 8.20 |
| Lysine | 6.39 |
| Leucine | 5.58 |
| Valine | 5.41 |
| Isoleucine | 5.18 |
| Threonine | 4.23 |
| Tyrosine | 4.19 |
| Serine | 3.46 |
| Proline | 2.62 |
| Arginine | 2.60 |
| Phenylalanine | 2.51 |
| Methionine | 1.56 |
| Histidine | 1.30 |
| Cysteine | 0.16 |

5. Pattern of disc electrophoresis

Figure 1:
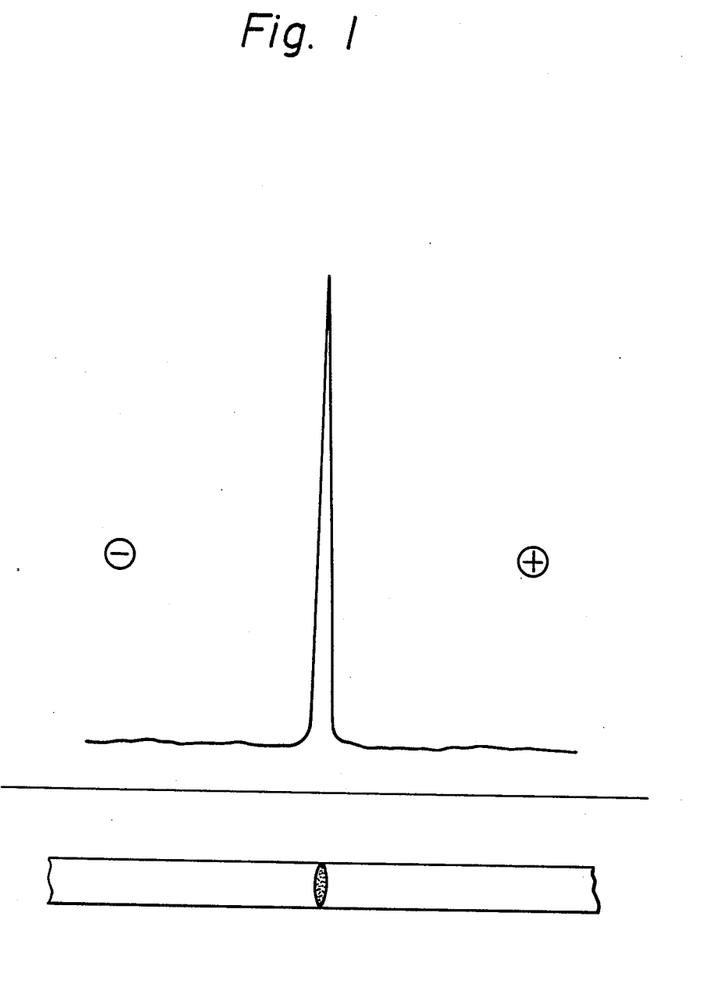
FIG. 1 illustrates a polyacrylamide gel electrophoretic profile of the CRP protein of the present invention.

Disc electrophoretic analyses of the CRP protein 25 $\mu g$) were performed on polyacrylamide gels (7% polyacrylamide) in Tris-glycine buffer (pH 8.3) at 4 mA/gel for 2.5 hours. A sharp protein band of the sample was obtained at a distance of 4.2±0.2 cm from the anode. The figure of the gell and the densitometric pattern of the electrophoresis are illustrated in FIG. 1.

6. Physiological characteristics

The CRP protein has an activity to reduce the blood cholesterol in mammals by oral administration.

This activity is stable in the range of at least −80° C. to 115° C. and pH 4.1 to 10.9, when the CRP protein is stored.

Pharmacological actions of the CRP protein

1. Pharmacological effects

As shown in each example hereinbelow, the present antiatherosclerotic drug that is composed of the CRP protein of the present invention can make an extremely effective reduction of the blood cholesterol in mammals. Accordingly, this drug is useful as a therapeutic or preventive medicine for hyperlipidemia, atherosclerosis and hypertension.

The preparation of the present invention can be used in mammals by means of oral, intraperitoneal, and intravenous administration and by other administration routes. The amount per usage is about 1 $\mu g$ to 1 g/kg body weight. The oral administration of about 0.1 mg to 100 mg/kg body weight is preferred. Any drug form of the present invention can be chosen and used as a solution in physiological saline and others, injections, powder made by lyophilization etc., suppository, entericcoated tablets, sublingual tablets, granules, tablets, capsules, etc. with appropriate carriers (e.g., starch, dextrin), diluent bases (e.g., calcium carbonate, lactose), diluents (e.g., physiological saline, distilld water) etc.

2. Acute toxicity

As shown in the examples hereinbelow, an $LD_{50}$ of the CRP protein according to the present invention is more than 802 mg/kg body weight, intraperitoneally in mice. The substance is substantially nontoxic on oral administration.

EXAMPLES

The present invention will now be further shown by, but is by no means limited to, the following examples.

Example 1

Preparation and purification of the CRP protein

*Streptococcus faecium* ADV1009 (FERM BP-296) was inoculated into 2 of Rogosa broth medium at a final concentration of $1 \times 10^6$ bacterial cells/ml. The inoculated medium was incubated at 37° C. for 10 hrs without agitation under an aerobic condition to yield $10^9$ bacterial cells/ml of culture broth. The bacterial cells were harvested by continuous centrifugation at 12,000 rpm, washed with physiological saline (0.85% NaCl), and suspended in the same solution to obtain 100 ml of the cell suspension at the concentration of $2 \times 10^{10}$/ml.

The above bacterial cell suspension was heat-treated at 115° C. for 10 minutes and treated 3 times with chloroform-methanol (2:1, v/v) to remove fats.

The defatted bacterial suspension was centrifuged at 3,000 rpm for 10 minutes and the lower layer, i.e., chloroform layer, was discarded. The aqueous layer was employed as a starting material for the following purification steps.

The starting material was then treated with 20 mg of pronase (Sigma protease type XIV) in 100 ml of phosphate buffer (pH 7.8) containing 0.0015 M $CaCl_2$ at 47° C. for 24 hours, and further treatment with 10 mg of pronase was carried out under the same conditions. The experimental conditions of the treatment with pronase are referred to and described in 'Methods in Enzymology' Vol. VIII, p. 26 (1966).

The material treated with pronase was divided into precipitation and supernatant fractions by centrifugation at 3,000 rpm for 10 minutes. The supernatant fraction was added with 1/9 volume of 100% (w/v) trichloroacetic acid (TCA), stood at 4° C. for 3 hours with agitation, and then centrifuged at 3,000 rpm for 10 minutes to obtain the precipitation and supernatant fractions. The precipitation fraction was added with the same volume of 10% TCA and the same process was repeated. The obtained precipitation was washed 3 times with ethyl ether to remove TCA, dissolved in 50 ml of distilled water, neutralized with 1 N NaOH, dialyzed to remove TCA completely, and finally centrifuged to yield 345 mg (dry weight) of the precipitation fraction.

The obtained precipitation fraction (345 mg) was added with 5 ml of 0.1 M Tris-acetate buffer (pH 8.0), 1 ml of 0.1 M magnesium acetate, and 0.06 ml of deoxyribonuclease (2 mg/ml deoxyribonuclease I (Sigma)), and incubated at 37° C. for 1 hour. Then, the reaction mixture was dialyzed against distilled water, using cellulose tube (Cellotube, Nakarai Kagakuyakuhin Co., Ltd., Japan) dialyzing substances smaller than 3,500 of molecular weight for 3 days. The dialyzed fraction was evaporated to dryness. The obtained material was then suspended in 5 ml of 0.05 M acetate buffer (pH 4.6) containing 440 units of ribonuclease $T_2$ (Sigma), incubated at 37° C. for 3 hours, and dialyzed against distilled water. The dialyzed fraction (molecular weight >20,000) was designated as Purified fraction I (dry weight 285 mg).

The above Purified fraction I was treated again with ribonuclease $T_2$ and dialyzed to obtain Purified fraction II (dry weight 274 mg). This fraction (II) was applied to a Toyopearl HW 55 column chromatograph equilibrated with 25 mM of Tris-HCl buffer (pH 7.5) containing 0.3 M NaCl. The column chromatogram of the fraction (II) by 1 ml/min of elution rate is shown in FIG. 2; line A shows protein content by absorbance at 280 nm; line B shows the nucleic acid content by absorbance at 260 nm; and line C shows the sugar content by the phenol-$H_2SO_4$ method.

Portion eluted later than dotted line D in FIG. 2 (elution volume 67 ml) was treated with ammonium sulfate (55% saturation) and Purified fraction III (dry weight 205.5 mg) was obtained from the supernatant of the ammonium sulfate fractionation fluid.

Figure 2:
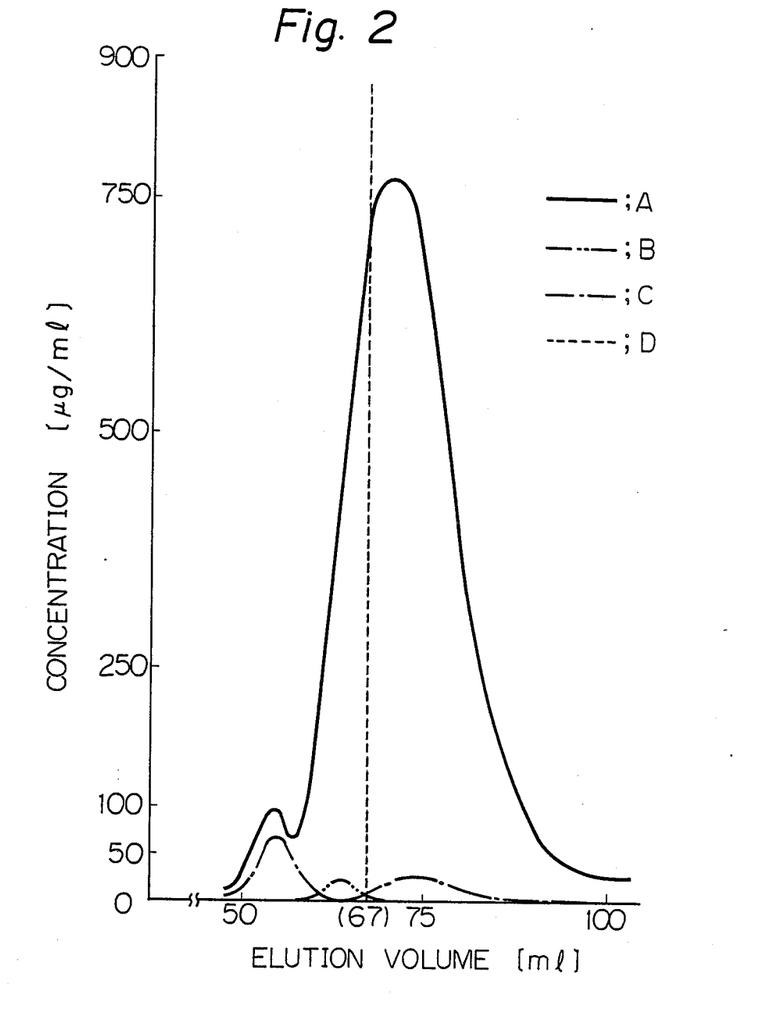
FIGS. 2 to 4 illustrate the elution patterns of gel filtration in Example 1 set forth hereinafter.
Figure 3:
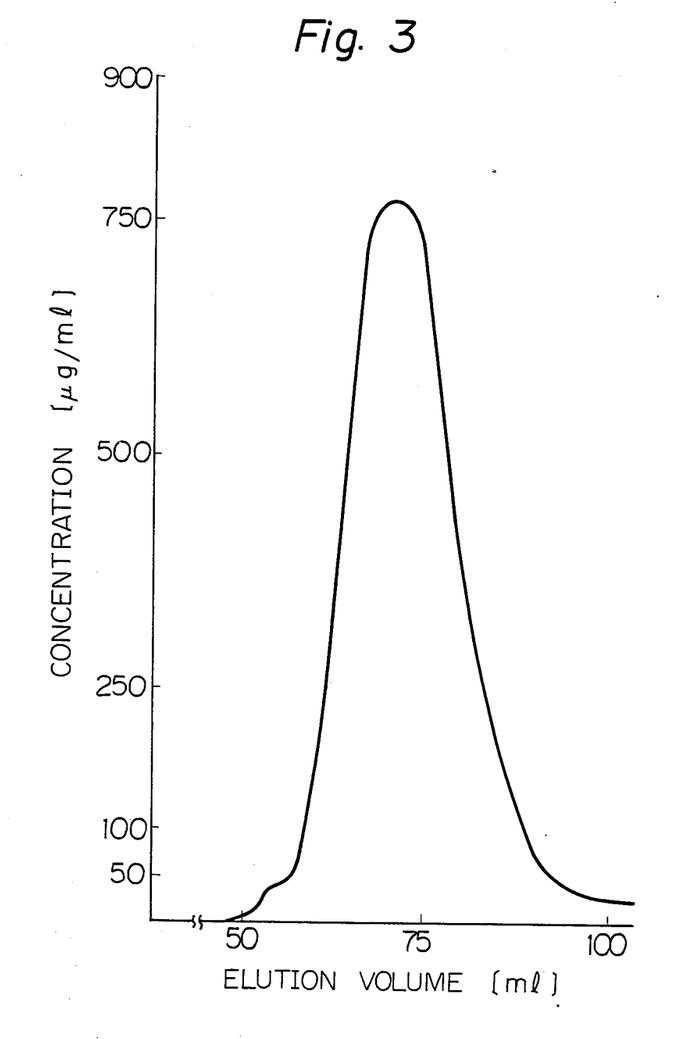

FIG. 3 shows the column chromatogram of purified fraction III under the same experimental conditions as shown in FIG. 2.

Figure 4:
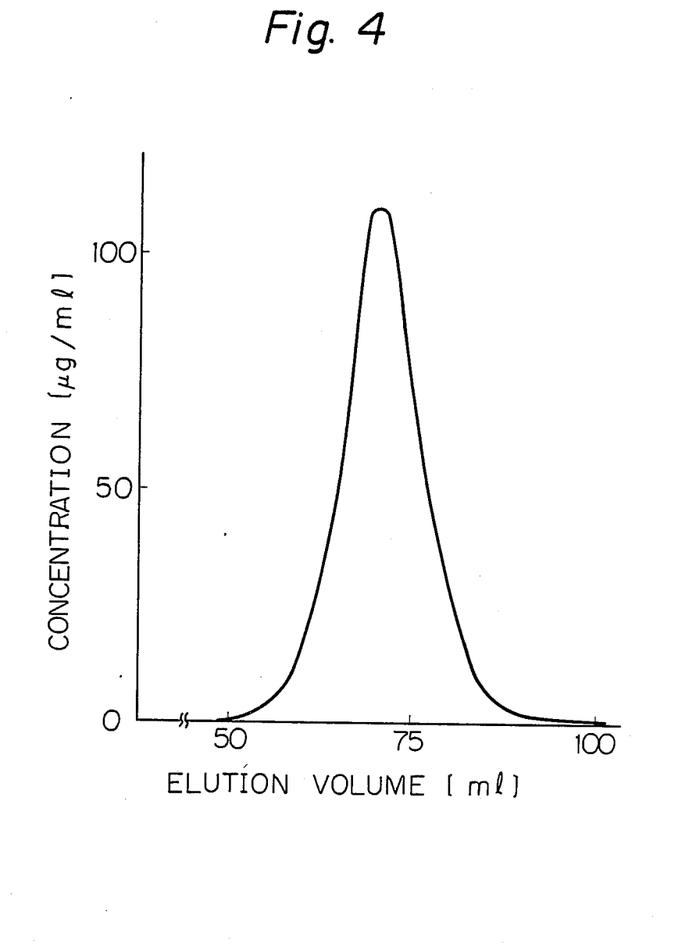

Since this fraction (III) contains a trace amount of sugars, the fraction was treated 3 times with 10% TCA and dialyzed under the same experimental conditions, and the finally purified CRP protein was obtained (dry weight 197.3 mg). The column chromatogram of the CRP protein under the same experimental conditions as in FIGS. 2 and 3 is shown in FIG. 4. The physicochemical characteristics of the CRP protein are shown above.

Table 4 shows the yield and the amounts of protein by Lowry's method, RNA by the orcinol method, DNA by the diphenylamine method, and sugars by the phenol-$H_2SO_4$ method in each preparation process. Values in the table indicate dry weight (mg).

TABLE 4

| Fractions | Yield | Protein | RNA | DNA | Sugars | Specific activity |
|---|---|---|---|---|---|---|
| Precipitation | 345 | 265.9 | 43.6 | 6.3 | 14.3 | 9.1 |
| Purified fraction I | 285 | 260.1 | 11.3 | 1.2 | 12.1 | 11.7 |
| Purified fraction II | 274 | 258.3 | 3.6 | 0.8 | 11.2 | 11.8 |
| Purified fraction III | 205.5 | 202.6 | trace | trace | 2.9 | 16.9 |
| CRP protein | 197.3 | 197.3 | trace | trace | trace | 17.6 |

The specific activity shown in Table 4 indicates the relative activity of cholesterol reduction by each fraction in conventional rats per unit weight, where that of the heat-treated bacterial cells mentioned above is 1. Assay methods for hypocholesterolemic activity in animal experiments are shown below in Example 2.

Besides, it was confirmed that the CRP protein can be separated and purified from other bacterial strains listed in Table 1, as well as in this example, but with a little variety of the yield.

Example 2

Pharmacological effect of the CRP protein

1. Hypocholesterolemic activity (1)

Physiological saline samples containing the equivalent to 50 mg/kg body weight of the lyophilized CRP protein were prepared. These samples were orally administered at a daily dosage of 1 ml to conventional rats (18 week-old male, average body weight of 246 g, 10 rats in each group) and conventional and germfree mice (18 week-old male, average body weight of 30 g, 10 mice in each group). The rats and mice were bred for 8 to 12 weeks. The arterial blood was then collected from the abdominal aorta of these animals and the serum samples were separated by centrifugation from the whole blood. The cholesterol was determined by Zurkowski's method (Choleskit, Kanto Kagaku K.K., Japan).

The results are summarized in Table 5. The values listed in the table are the reduction rate (%) from the values of the control groups to which no sample is dosed. The composition (% by weight) of the diet, given ad libitum, is shown in Table 6.

TABLE 5

| Animals | Reduction rate (%) |
|---|---|
| Conventional rats (12 weeks) | 25.2 ± 0.7 |
| Conventional mice (8 weeks) | 33.5 ± 1.1 |
| Germfree mice (8 weeks) | 21.7 ± 0.9 |

TABLE 6

| Composition | Weight % |
|---|---|
| Casein | 20 |
| Soybean oil | 10 |
| Wheat starch | 61 |
| Minerals | 4 |
| Vitamin mixture | 2 |
| Powdered filter paper | 3 |

2. Hypocholesterolemic activity (2)

The above-mentioned samples were orally administered at a daily dosage of 1 ml to conventional rats (18 week-old male, average body weight of 238 g, 15 rats in each group) and conventional and germfree mice (18 week-old male, average body weight of 31 g, 10 mice in each group) for 12 weeks. The blood cholesterol was determined as mentioned above. The results are shown in Table 7.

The terms 'cholesterol-loaded' and 'fructose-loaded' in the table mean the addition of 1% cholesterol into the above-mentioned diet and the substitution of fructose for the total amount of wheat starch in the above-mentioned diet, respectively. The values in the table are the reduction rate (%) from the values of the no-dosage control group.

TABLE 7

| Animals | Reduction rate (%) |
|---|---|
| Germfree mice*[1] | 35.4 ± 1.3 |
| Conventional mice*[1] | 38.9 ± 0.7 |
| Conventional rats*[1] | 49.2 ± 1.1 |
| Conventional rats*[2] | 41.5 ± 1.3 |

*[1]Cholesterol-loaded diet
*[2]Fructose-loaded diet

3. Hypocholesterolemic activity (3)

Physiological saline samples containing 10 mg/ml of the CRP protein were orally administered at a daily dosage of 1 ml per rat for 2 weeks to hypercholesterolemic rats (18 week-old male, average body weight of 250 g, 5 rats in each group) fed with 'cholesterol-loaded' diet. The blood cholesterol was determined as mentioned above. The results are shown in Table 8. The value of the administration group is the cholesterol reduction rate (%) to the control group to which no sample is dosed.

TABLE 8

| Animals | Reduction rate (%) |
|---|---|
| Administered | 49.9 |
| Control | 0 |

4. Dose response

Physiological saline samples containing 0.1 mg–20 mg/ml of the CRP protein were orally administered at a daily dosage of 1 ml per rat to conventional rats (6 week-old male, average body weight of 216 g, 5 rats in each group) for 4 weeks. The blood cholesterol was determined as mentioned above (control group was dosed with no sample). The results were shown in Table 9.

TABLE 9

| Dosage (mg/rat) | Reduction rate (average %) |
|---|---|
| Control | 0 |
| 0.1 | 9.8 ± 0.7 |
| 1 | 14.3 ± 1.2 |
| 10 | 47.9 ± 1.1 |
| 20 | 51.1 ± 0.9 |

5. Acute toxicity

Physiological saline samples (0.5 ml/mouse) containing 1, 10, and 100 mg of the CRP protein were intraperitoneally administered to ICR mice (6 week-old male, average body weight of 31.4±0.6 g, 10 mice in each group). The thanatobiologic observation of the mice was carried out for 14 days. A control material was physiological saline.

The $LD_{50}$ value calculated according to Behrens-Kärber method was more than 802 mg/kg body weight. The substance was substantially nontoxic on oral administration.

6. Pharmaceutical preparations (1) A 50 mg amount of the purified CRP protein was uniformly mixed with 250 mg of purified starch powder and, then, the tablets were formed for oral administration. This tablet corresponds to a dosage of $10^{10}$ heat-treated cells/kg body weight for an adult having a body weight of 50 kg.

(2) The CRP protein could be uniformly mixed with diluent bases such as calcium carbonate, lactose, etc., lubricants such as stearic acid, talcum, etc., and other additives and the tablets can be then formed for oral administration. This tablet corresponds to a daily dosage of 0.1 mg–100 mg/kg body weight.

(3) The CRP protein (900 mg) was suspended and dissolved in distilled water (30 ml) sweetened with syrup and, then, the syrups were formed.

We claim:

1. A hypocholesterolemically active protein wherein said protein is derived from a microoganism belonging to the genus *Streptococcus* and has the following characteristics:

(a) Molecular weighyt by gel filtration: 30,000±7,000
(b) Isoelectric point: 7.9±0.2
(c) Amino acid composition (mole %):

| | | | |
|---|---|---|---|
| Glycine | 25.23 | Alanine | 10.98 |
| Glutamate | 10.34 | Asparaginate | 8.20 |
| Lysine | 6.39 | Leucine | 5.58 |
| Valine | 5.41 | Isoleucine | 5.18 |
| Threonine | 4.23 | Tyrosine | 4.19 |
| Serine | 3.46 | Proline | 2.62 |
| Arginine | 2.60 | Phenylalanine | 2.51 |

-continued

| Methionine | 1.56 | Histidine | 1.30 |
| --- | --- | --- | --- |
| Cysteine | 0.16 | | |

(d) Pattern of electrophoresis: a sharp band on the anode side on polyacrylamide gel electrophoresis (e) Physiological characteristics: having a hypocholesterolemic activity when orally administered to mamuals.

2. A hypocholesterolemically active protein as claimed in claim 1, wherein said microorganism is selected from the group consisting of S. faceium, S. faeccalis, S. avium, S. bovis, S. salivarius, S. durans, S. mitis and S. equinus.

3. A hypocholesterolemically active protein as claimed in claim 1, wherein said microoganism is selected from the group consisting of S. faecium FERM BP-296, S. faecalis FERM BP-297, S. avium FERM BP-298, S. salivarius FERM BP-299, S. durans FERM BP-300, S. mitis FERM BP-301 and S. equinus FERM BP-302.

4. A hypocholesterolemic or antiatherosclerotic pharmaceutical composition which comprises a hypocholesterolemically effective amount of a protein as claimed in claim 1 and a pharmaceutically acceptable carrier therefor.

5. A hypocholesterolemic or antiatherosclerotic pharmaceutical composition which comprises a hypochloesterolemically effective amount of a protein as claimed in claim 2 and a pharmaceutically acceptable carrier therefor.

6. A hypocholesterolemic or antiatherosclerotic pharmaceutical composition which comprises a hypocholesterolemically effective amount of a protein as claimed in claim 3 and a pharmaceutically acceptable carrier therefor.

7. A method for reducing the blood cholesterol in mammals comprising orally administering to a mammal in need thereof a hypocholesterolemically effective amount of a protein as claimed in claim 1.

8. A method for reducing the blood cholesterol in mammals comprising orally administering to a mammal in need thereof a hypocholesterolemically effective ammount of a protein as claimed in claim 2.

9. A method for reducing the blood cholesterol in mammals comprising orally administering to a mammal in need thereof a hypocholesterolemically effective amount of a protein as claimed in claim 3.

* * * * *